(12) United States Patent
Cook et al.

(10) Patent No.: US 12,051,499 B2
(45) Date of Patent: Jul. 30, 2024

(54) INVENTORY SYSTEMS AND METHODS FOR DETECTING AND COUNTING POTENTIALLY RETAINED SURGICAL ITEMS

(71) Applicant: Covidien LP, Mansfield, MA (US)

(72) Inventors: Henry D. Cook, Lyons, CO (US); Lewis R. Puterbaugh, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 408 days.

(21) Appl. No.: 17/411,608

(22) Filed: Aug. 25, 2021

(65) Prior Publication Data

US 2023/0060843 A1    Mar. 2, 2023

(51) Int. Cl.
| | |
|---|---|
| *H04W 64/00* | (2009.01) |
| *A61B 90/98* | (2016.01) |
| *G06K 19/07* | (2006.01) |
| *G06K 19/077* | (2006.01) |
| *G16H 40/20* | (2018.01) |
| *H04W 4/02* | (2018.01) |
| *H04W 4/80* | (2018.01) |

(52) U.S. Cl.
CPC ............. *G16H 40/20* (2018.01); *A61B 90/98* (2016.02); *G06K 19/0708* (2013.01); *G06K 19/07758* (2013.01); *G06K 19/07786* (2013.01); *H04W 4/80* (2018.02)

(58) Field of Classification Search
CPC ......... G16H 40/20; A61B 90/98; H04W 4/80; G06K 19/0708; G06K 19/07758; G06K 19/07786
See application file for complete search history.

(56) References Cited

U.S. PATENT DOCUMENTS

| | | | |
|---|---|---|---|
| 2004/0250819 A1 | 12/2004 | Blair et al. | |
| 2006/0187044 A1* | 8/2006 | Fabian | A61B 5/06 340/572.1 |
| 2015/0216610 A1 | 8/2015 | Augustine | |
| 2016/0206399 A1 | 7/2016 | Blair | |

FOREIGN PATENT DOCUMENTS

| | | |
|---|---|---|
| EP | 3235463 A1 | 10/2017 |
| WO | 2006086603 A2 | 8/2006 |

OTHER PUBLICATIONS

Extended European Search Report dated Jan. 11, 2023 corresponding to counterpart Patent Application EP 22191672.9.

* cited by examiner

*Primary Examiner* — Moustapha Diaby
(74) *Attorney, Agent, or Firm* — Carter, DeLuca & Farrell LLP

(57) ABSTRACT

An inventory system configured for detecting and counting potentially retained surgical items within a body of a patient includes a tag configured to transmit a return signal including an electrical characteristic when energized, a signal generator configured to generate an energizing signal for the tag, an antenna operably coupled to the signal generator and configured to receive at least the return signal transmitted by the tag, a processor, and a memory. The memory includes instructions stored thereon, which, when executed by the processor, cause the inventory system to energize the tag by the energizing signal, receive the return signal from the tag by the antenna, and determine a presence of the beacon tag based on the electrical characteristic.

17 Claims, 6 Drawing Sheets

INVENTORY SYSTEMS AND METHODS FOR DETECTING AND COUNTING POTENTIALLY RETAINED SURGICAL ITEMS

FIELD

The present disclosure relates generally to interrogation and detection systems for radio-frequency (RF) tags, and more particularly, detection and inventory systems for potentially retained surgical items within surgical sites.

BACKGROUND

It is often useful to determine whether objects associated with a surgery are present in a patient's body before completion of the surgery. Such objects may take a variety of forms. For example, the objects may take the form of instruments, for instance, scalpels, scissors, forceps, hemostats, and/or clamps. Also, for example, the objects may take the form of related accessories and/or disposable objects, for instance, surgical sponges, gauzes, and/or pads. Failure to locate an object before closing the patient may require additional surgery, and in some instances, may have unintended medical consequences.

Accordingly, there is a need for a technology that is capable of providing both presence detection and tagged surgical item/implement identification functionality in the medical setting, as well as inventory controls of the tagged items/implements. Specifically, detecting the presence of, identifying, and maintaining inventory of tagged surgical items and materials that are used during the execution of a medical procedure. Technologies exist that enable these functions both individually as well as in conjunction with each other, but the methods and packaging of the discrete solutions used are not ideal for the application. More specifically, the components attached or affixed to the items being tracked are either too large physically and present nuisances or obstacles in the execution of the procedure, or the detection and identification performance of the solution may degrade rapidly in the presence of variable and uncontrolled dielectric or conductive materials.

Accordingly, there are needs for improvements in presence detection, tagged item identification, and inventory functionality in the medical setting.

SUMMARY

This disclosure relates to systems for detection of surgical items and/or devices used in body cavities during surgery, specifically systems that include an antenna to be inserted directly into a surgical site to detect such surgical items and/or devices.

In accordance with aspects of the disclosure, an inventory system configured to detect and count potentially retained surgical items within a body of a patient includes a beacon tag configured to transmit a first return signal when energized, a signal generator configured to generate an energizing signal for the beacon tag, an antenna operably coupled to the signal generator, a processor, and a memory. The first return signal includes an electrical characteristic. The antenna is configured to receive the first return signal transmitted by the beacon tag. The memory includes instructions stored thereon, which when executed by the processor cause the system to energize the beacon tag by the energizing signal, receive the first return signal from the beacon tag by the antenna, and determine a presence of the beacon tag based on the electrical characteristic.

In an aspect of the present disclosure, the electrical characteristic may be a resonant frequency of the beacon tag.

In another aspect of the present disclosure, the electrical characteristic may be a ring-down decay rate of the beacon tag.

In yet another aspect of the present disclosure, the system may include an RFID tag configured to transmit a second return signal including the electrical characteristic when energized.

In a further aspect of the present disclosure, the instructions, when executed by the processor, may further cause the system to store a value of the electrical characteristic of the first return signal in the memory of the RFID tag.

In yet a further aspect of the present disclosure, the RFID tag may include a unique identifier, and the instructions, when executed by the processor, may further cause the system to associate the value of the electrical characteristic with the unique identifier.

In an aspect of the present disclosure, the instructions, when executed by the processor, may further cause the system to determine an identity of the potentially retained surgical item based on the association between the value of the electrical characteristic and the unique identifier.

In yet another aspect of the present disclosure, the system may further include a display. The instructions, when executed by the processor, may further cause the system to display the determined presence of the beacon tag on the display.

In a further aspect of the present disclosure, the instructions, when executed by the processor, may further cause the system to determine a quantity of potentially retained surgical items based on the first return signal.

In yet a further aspect of the present disclosure, the RFID tag may include at least one of a high frequency tag, or an ultra-high frequency tag.

In accordance with aspects of the disclosure, a computer-implemented method is provided for detecting and counting potentially retained surgical items within a body of a patient. The method includes energizing a beacon tag that is configured to transmit a first return signal, receiving the first return signal from an antenna, the antenna operably coupled to a signal generator, and determining a presence of the beacon tag based on the electrical characteristic. The first return signal includes an electrical characteristic when energized. The antenna is configured to receive the first return signal transmitted by the beacon tag.

In another aspect of the present disclosure, the electrical characteristic may be a resonant frequency of the beacon tag.

In yet another aspect of the present disclosure, the electrical characteristic may be a ring-down decay rate of the beacon tag.

In a further aspect of the present disclosure, the method may further include displaying the determined presence of the beacon tag on a display.

In yet a further aspect of the present disclosure, the method may further include transmitting a second return signal, by an RFID tag, the second return signal including the electrical characteristic when energized.

In a further aspect of the present disclosure, the method may further include storing a value of the electrical characteristic of the first return signal in the memory of the RFID tag.

In an aspect of the present disclosure, the RFID tag may include a unique identifier, and the method may further include associating the value of the electrical characteristic with the unique identifier.

In yet another aspect of the present disclosure, the method may further include displaying an identity of the potentially retained surgical item on a display based on the association between the value of the electrical characteristic and the unique identifier.

In another aspect of the present disclosure, the method may further include determining a quantity of potentially retained surgical items based on the first return signal.

In accordance with aspects of the disclosure, a non-transitory computer-readable medium is provided. The non-transitory computer-readable medium stores instructions which, when executed by a processor, cause the processor to perform a method for detecting and counting potentially retained surgical items within a body of a patient. The method includes energizing a beacon tag, the beacon tag configured to transmit a return signal including an electrical characteristic when energized, receiving the return signal from an antenna, the antenna operably coupled to a signal generator, the antenna configured to receive the return signal transmitted by the beacon tag, and determining a presence of the beacon tag based on the electrical characteristic.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements and have been solely selected for ease of recognition in the drawings.

Various aspects of the presently disclosed inventory systems are described hereinbelow with reference to the drawings.

DETAILED DESCRIPTION

In the following description, certain specific details are set forth in order to provide a thorough understanding of disclosed aspects. However, one skilled in the relevant art will recognize that aspects may be practiced without one or more of these specific details or with other methods, components, materials, etc. In other instances, well-known structures associated with transmitters, receivers, or transceivers have not been shown or described in detail to avoid unnecessarily obscuring descriptions of the aspects.

Reference throughout this specification to "one aspect" or "an aspect" means that a particular feature, structure, or characteristic described in connection with the aspect is included in at least one aspect. Thus, the appearances of the phrases "in one aspect" or "in an aspect" in various places throughout this specification are not necessarily all referring to the same aspect. Furthermore, the particular features, structures, or characteristics may be combined in any suitable manner in one or more aspects.

Figure 1:
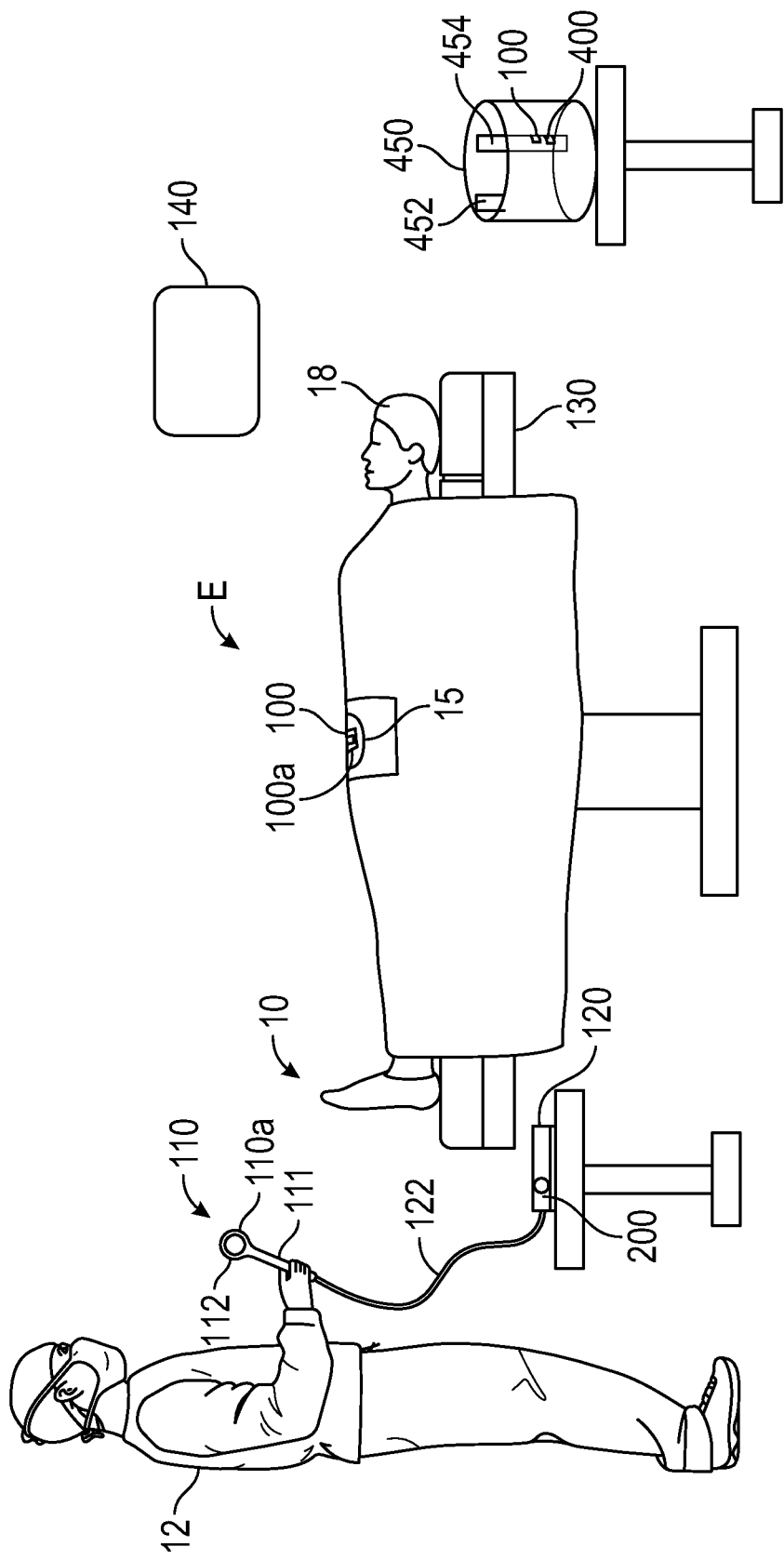
FIG. 1 is a schematic diagram showing a surgical environment illustrating a medical provider using an inventory system for detecting and counting an object within a patient that is tagged with an RFID tag according to one illustrated aspect.

FIG. 1 depicts a surgical environment "E" in which a medical provider 12 operates an inventory system 10 for detection and counting of beacon tags 400 and/or radio-frequency identification (RFID) tags 100 to ascertain the presence or absence of items, implements, or objects 100a (and, potentially, packaged surgical objects 454 one used) in a patient 18. The inventory system 10 may include a signal generator 120 and an antenna 110 coupled to the signal generator 120 by one or more communication paths, for example, coaxial cable 122. In one aspect of the inventory system 10, the antenna 110 may take the form of a hand-held wand 110a.

The object 100a may take a variety of forms, for example, instruments, accessories, and/or disposable objects useful in performing surgical procedures. For instance, the object 100a may take the form of scalpels, scissors, forceps, hemostats, and/or clamps. Also, for example, the objects 100a may take the form of surgical sponges, gauze, and/or padding. The object 100a is tagged, carrying, attached, or otherwise coupled to an RFID tag 100. Aspects of the inventory system 10 disclosed herein are particularly suited to operate with one or more RFID tags 100, which are not accurately tuned to a chosen or selected resonant frequency.

In use, the medical provider 12 may position the wand 110a proximate the patient 18 in order to detect the presence or absence of the one or more RFID tags 100 and hence an object 100a. The medical provider 12 may, in some aspects, move the wand 110a along and/or across the body of the patient 18. For a detailed description of an exemplary inventory system, reference may be made to commonly owned U.S. Patent Application Publication No. 2004/0250819 to Blair et al., entitled "Apparatus and Method for Detecting Objects Using Tags and Wideband Detection Device," filed Mar. 29, 2004, the entire contents of which is hereby incorporated by reference herein.

The inventory system 10 may include a display 140 configured to display images and/or other data. The inventory system 10 may include an imaging device 111 configured to capture an image of an area, the area including at least a portion of a body of the patient 18.

As seen in FIG. 1, inventory system 10, for detection and counting of surgical implements (e.g., object 100a) within a patient's body 18, includes a signal generator 120 to provide an energizing signal for a beacon tag 400 and/or one or more RFID tags 100 affixed to an object 100a. Each RFID tag 100 is configured to transmit a return signal when energized, such that an antenna 110 can detect the return signal and confirm the presence of objects 100a within the body of patient 18. The antenna 110 is operably coupled to the signal generator 120 via a communication cable 122, which may be of variable length to provide greater range of motion to the clinician handling the antenna 110. The signal generator 120 may include a controller 200.

Figure 2:
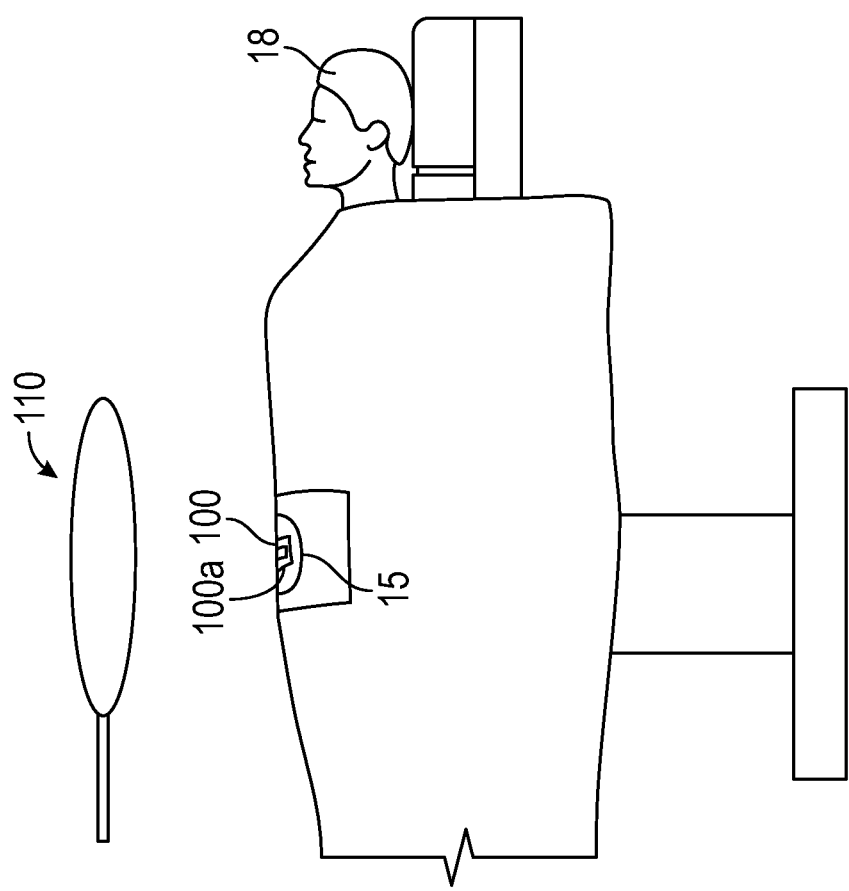
FIG. 2 is a schematic illustration of an antenna for detection of surgical implements within a patient's body in active use within a surgical site.

In one aspect of inventory system 10, the antenna 110 is an antenna 110 configured to be waved over the surgical site 15, e.g., over the body of patient 18. As seen in FIG. 2, for example, the antenna 110 may be held over the body of the patient 18 at the height of about four or about five inches while attempting to detect beacon tags 400 and/or RFID tags 100, so that the user may detect and/or confirm the presence of objects 100a (and/or surgical object 454 once used in the surgical procedure) within the body of patient 18.

As seen in FIGS. 1 and 2, the inventory system 10 may further include an RFID-enabled secure package 450 (e.g., RFID-enabled smart packaging and/or RFID enabled secure mutual authentication packaging), which includes an RFID tag 452 affixed thereto. For example, an RFID tag may be secured to a lid or a body of the RFID-enabled secure package 450. The RFID tag 452 is configured to transmit a return signal when energized. Generally, the RFID-enabled secure package 450 will include an as-yet unused surgical object 454 configured to be removed from the RFID-enabled secure package 450. The surgical object 454 includes a beacon tag 400 and/or a retained surgical item RFID tag, e.g., the RFID tag 100, affixed to the surgical object 454. The surgical object 454 may include, for example, any surgical sponge, cotton swab, instrument, tool, and/or device that is unintentionally left in the patient at the completion of a surgery or other procedure.

The RFID-enabled secure package 450 includes, but is not limited to, for example, caps and closures and are generally configured to verify the contents of sealed containers to ensure the product is genuine, not part of a recall, within the expiration date, and/or has not been tampered with or diverted. RFID-enabled secure package 450 generally includes a secure package RFID tag 452.

In aspects, the retained surgical item RFID tag 100 may be linked to the secure package RFID tag 452 by embedding an encrypted block of data that contains the unique identifier of the RFID tag 100. For example, to enable the use of the retained surgical object 454, the RFID tag 100 may be scanned by the antenna 110 in the inventory system 10.

Figure 3:
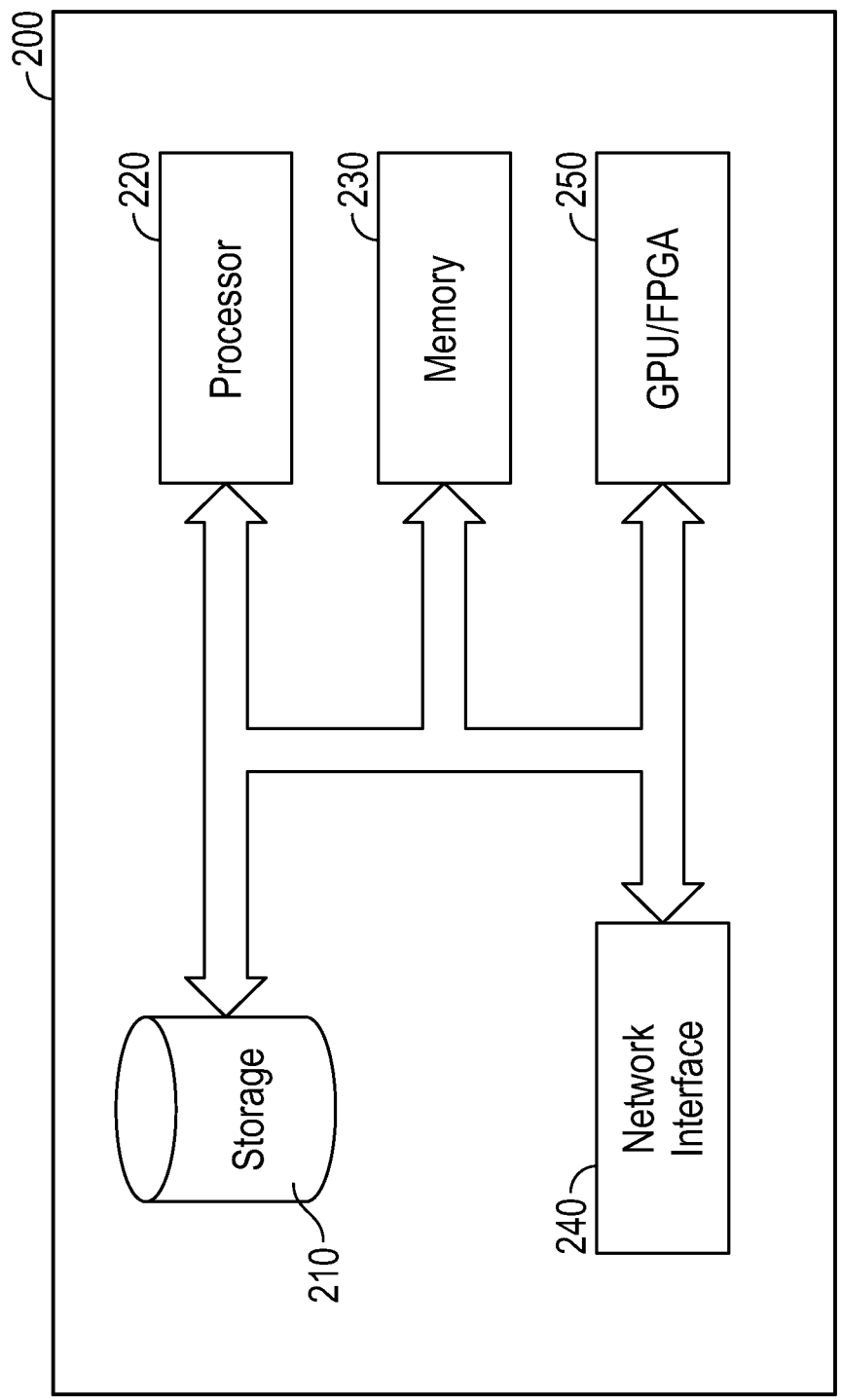
FIG. 3 is a block diagram of a controller of the inventory system of FIG. 1.

FIG. 3 illustrates that controller 200 includes a processor 220 connected to a computer-readable storage medium or a memory 230. The computer-readable storage medium or memory 230 may be a volatile type of memory, e.g., RAM, or a non-volatile type of memory, e.g., flash media, disk media, etc. In various aspects of the disclosure, the processor 220 may be another type of processor such as, without limitation, a digital signal processor, a microprocessor, an ASIC, a graphics processing unit (GPU), a field-programmable gate array (FPGA), or a central processing unit (CPU). In certain aspects of the disclosure, network inference may also be accomplished in systems that have weights implemented as memristors, chemically, or other inference calculations, as opposed to processors.

In aspects of the disclosure, the memory 230 can be random access memory, read-only memory, magnetic disk memory, solid-state memory, optical disc memory, and/or another type of memory. In some aspects of the disclosure, the memory 230 can be separate from the controller 200 and can communicate with the processor 220 through communication buses of a circuit board and/or through communication cables such as serial ATA cables or other types of cables. The memory 230 includes computer-readable instructions that are executable by the processor 220 to operate the controller 200. In other aspects of the disclosure, the controller 200 may include a network interface 240 to communicate with other computers or to a server. A storage device 210 may be used for storing data.

Figure 4A:
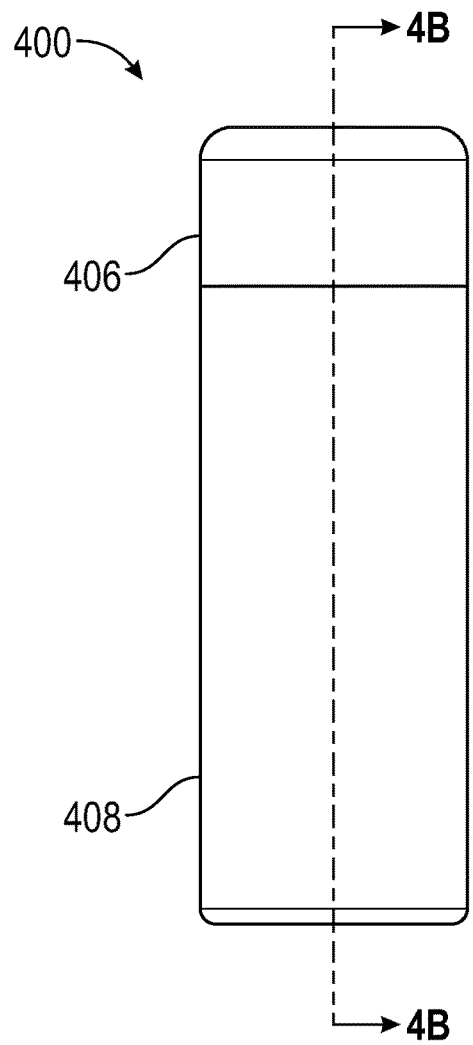
FIG. 4A is a side view of a beacon tag of the inventory system of FIG. 1.
Figure 4B:
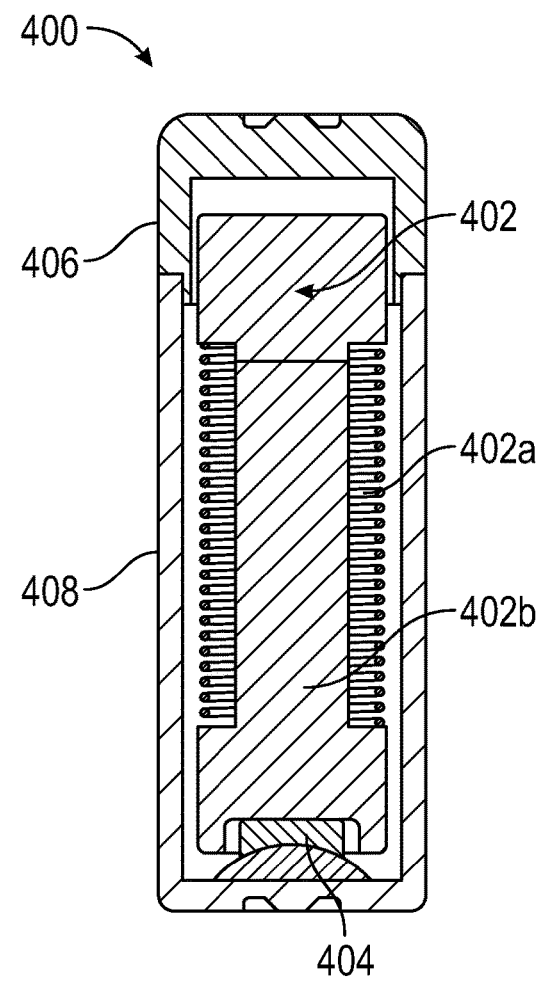
FIG. 4B is a longitudinal cross-sectional view of the beacon tag of FIG. 4A as taken through 4B-4B of FIG. 4A.

Referring to FIGS. 4A and 4B, beacon tag 400 generally includes an upper cover 406, a lower cover 408, an inductor 402, and a capacitor 404. The upper cover 406 and the lower cover 408 may both be constructed of a non-conductive material. The upper cover 406 and the lower cover 408 are configured to define a fluid tight cavity within which the inductor 402 and the capacitor 404 are retained. The inductor 402 generally includes a conductive wire 402a wrapped around a ferrite core 402b. The inductance of the inductor 402 is primarily determined by the ferrite core 402b, the number of turns of the conductive wire 402a around the ferrite core 402b, and a diameter (e.g., the gauge) of the conductive wire 402a. The capacitor 404 may be disposed below the inductor 402. The capacitor 404 may be disposed on a lower portion of the lower cover 408. The inductor 402 and the capacitor 404 form an L-C resonant circuit, which when energized resonate at a resonant frequency determined primarily by the capacitance and the inductance. Thus, the resonant frequency of beacon tag 400 may be calculated by $1/(2*\pi*\sqrt{(L*C)})$, wherein "L" is the inductance, and "C" is the capacitance.

Figure 5:
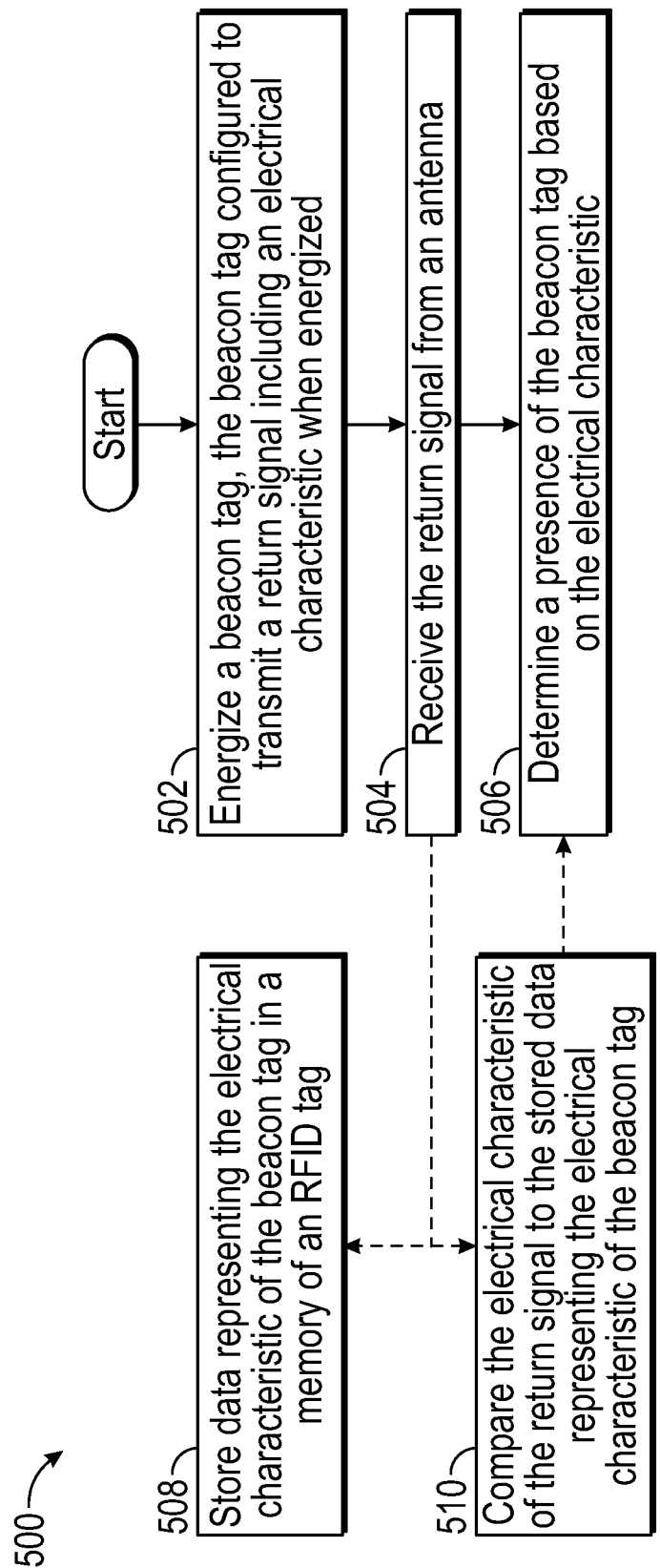
FIG. 5 is a flow chart of a computer-controlled method for detecting and counting potentially retained surgical items using the inventory system of FIG. 1.

FIG. 5 shows a flow chart of an exemplary computer-implemented method 500 for detecting and counting potentially retained surgical items within a body of a patient in accordance with aspects of the present disclosure. Although the steps of FIG. 5 are shown in a particular order, the steps need not all be performed in the specified order, and certain steps can be performed in another order. For simplicity, FIG. 5 will be described below, with the controller 200 performing the operations. However, in various aspects, the operations of FIG. 5 may be performed in part by the controller 200 of FIG. 3 and in part by another device, such as a remote server. These variations are contemplated to be within the scope of the present disclosure.

The two main functions of an inventory system (such as an operating room safety system) are to detect and count potentially retained surgical items (RSIs). The term retained surgical item, as used herein, includes any surgical sponge, instrument, tool, and/or device that is unintentionally left in the patient at the completion of a surgery or other procedure. The disclosed technology detects and counts potential RSIs, each of which includes a beacon tag 400, in a way that provides individual identification to each potential retained surgical item based on the beacon tag 400.

Initially, at step 502, the signal generator 120 energizes a beacon tag 400, using an antenna 110. The antenna 110 is configured to receive a return signal transmitted by the beacon tag 400. In an aspect, the beacon tag 400 may be attached to a surgical object 454 (e.g., surgical gauze and/or a surgical sponge).

Figure 6:
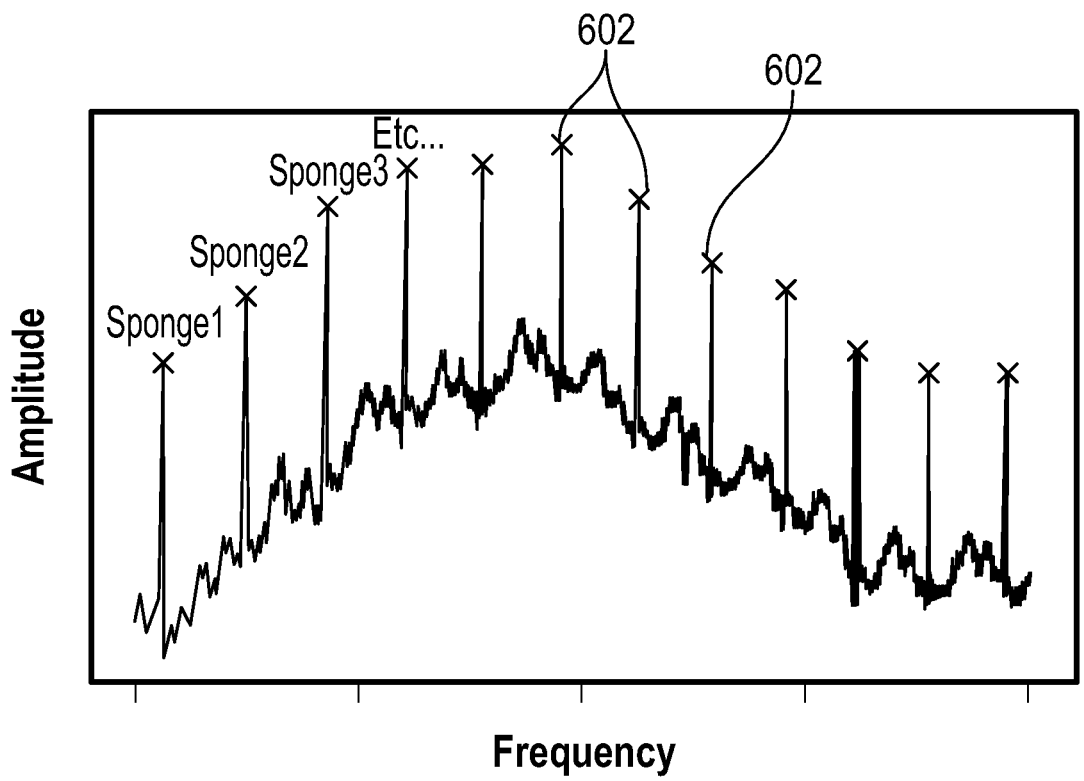
FIG. 6 is a graph of resonant frequencies of beacon tags of the inventory system of FIG. 1.

The return signal includes an electrical characteristic. The electrical characteristic may include a resonant frequency of the beacon tag 400 (e.g., about 127 kHz or about 140 kHz (FIG. 6)). The beacon tag 400 may include a resonant L-C circuit that when energized, resonates at the resonant frequency of the L-C circuit. In aspects, the resonant frequency may be set by tuning the inductance or the capacitance of the L-C circuit, and/or the resonant frequency may be a byproduct of the manufacturing tolerances of the inductor and the capacitor used in the L-C circuit of the beacon tag 400. For example, if the inductor 402 of the beacon tag 400 has a tolerance of about 5% and the capacitor 404 of the beacon tag 400 has a tolerance of about 5% then there may be a 10% range on the resonant frequency. The resonant frequency of the L-C circuit may be tuned, for example, by changing the number of turns of conductive wire 402*a* on the inductor 402 (e.g., removing a turn of conductive wire 402*a* to decrease the inductance) and/or by changing the value of the capacitor 404 (FIG. 4B). In aspects, multiple beacon tags 400 may resonate at different frequencies when energized by the antenna 110, each beacon tag 400 having a unique resonant frequency. At step 508, the unique resonant frequency of each beacon tag 400 (FIG. 6) may be measured in advance and stored in a memory 230 (or, for example, the memory of RFID tag 100) and associated with a specific unique surgical object 454.

Figure 7:
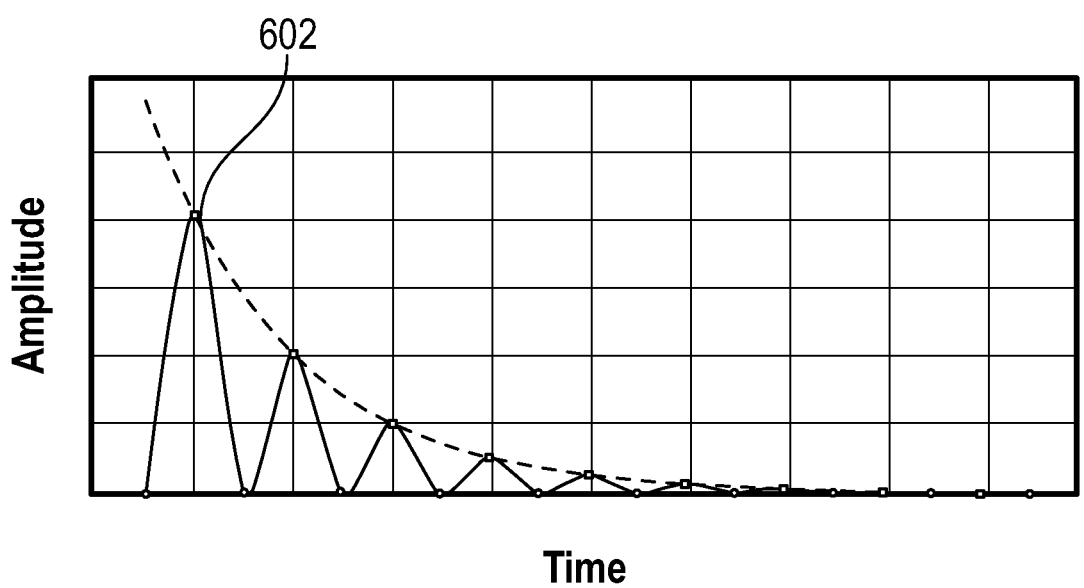
FIG. 7 is a graph of a ring-down decay of the beacon tag of the inventory system of FIG. 1.

In aspects, the electrical characteristic of the return signal includes a ring-down decay rate of the beacon tag 400. After activation, the amplitude of the resonant frequency of the beacon tag 400 tends to decay over time (FIG. 7). The decay over time of the amplitude of the resonant frequency is the ring-down decay rate of the beacon tag 400. By tracking peak values of the return signal as it decays over time, the ring-down decay rate may be determined (e.g., by slope detection). Each unique beacon tag 400 has a unique ring-down decay rate (and/or slope) (FIG. 7) and may be identified based on that unique ring-down decay rate. The ring-down decay rate of a particular beacon tag 400 may be stored in memory for later recall to identify that beacon tag 400. In aspects, a mask with upper and/or lower limits, may be applied to a waveform of the return signal to enable determining if the return signal is from a beacon tag 400.

In aspects, the inventory system 10 may include an RFID-enabled secure package 450 (e.g., smart packaging), which includes a set of manufactured potential RSIs 454 (such as cotton sponges). The RFID-enabled secure package 450 includes an RFID tag 452 (e.g., an RFID chip), which is capable of mutual authentication with a host (e.g., controller 200). The RFID tag 100 on the potential RSIs 454 may include a unique identifier.

Next, at step 504, the controller 200 receives the return signal from the antenna 110, which is configured to receive at least one return signal transmitted by the beacon tag 400. At step 510, the return signal may be compared to stored data representing the electrical characteristic of the beacon tag 400. If the stored data and the return signal include the same value electrical characteristic, the processor may determine an identity of a specific unique surgical object 100*a*, 454.

In aspects, the antenna 110 may include a sensor 112 (e.g., a gyro and/or a GPS), which is configured to provide localization-based data of the antenna 110 when scanning for the beacon tag 400. The spatial parameter may further include a proximity of the antenna 110 to a patient 18. The spatial parameter may be used to help determine the presence and/or location of a beacon tag 400.

Next, at step 506, the controller 200 determines a presence of the beacon tag 400 based on the electrical characteristic.

It is contemplated that the display 140 may be incorporated into the antenna 110, within a directly connected base station box, and/or may utilize a remotely connected display such as a remote screen or tablet.

In aspects, the processor may determine a quantity of potentially retained surgical objects 454 based on the presence of one or more the beacon tags 400. The quantity and the identity of each of the beacon tags 400 and/or surgical objects may be displayed.

In an aspect, an RFID tag 100 may be attached to the surgical object 454. The RFID tag 100 may include a high-frequency RFID tag, a low-frequency RFID tag, and/or an ultra-high frequency RFID tag. The RFID tag may include a unique identifier configured for identifying unique surgical objects. The processor may associate the value of the electrical characteristic with the unique identifier. The processor may determine an identity of the potentially retained surgical object 454 based on the association between the value of the electrical characteristic and the unique identifier. For example, the unique identifier may be a serial number of the RFID tag 100 which may be associated with a resonant frequency (of about 129 kHz) of the beacon tag 400 to identify a unique surgical sponge. The processor may display the determined identity of the potentially retained surgical item on a display 140 (FIG. 1).

While several aspects of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting but merely as exemplifications of particular aspects. Those skilled in the art will envision other modifications within the scope of the claims appended hereto.

What is claimed is:

1. An inventory system configured for detecting and counting potentially retained surgical items within a body of a patient, the inventory system comprising:
    a beacon tag configured to transmit a first return signal when energized, the first return signal including an electrical characteristic;
    a signal generator configured to generate an energizing signal for the beacon tag;
    an antenna operably coupled to the signal generator, the antenna configured to receive at least the first return signal transmitted by the beacon tag;
    an RFID tag configured to transmit a second return signal including the electrical characteristic when energized;
    a processor; and
    a memory, including instructions stored thereon, which when executed by the processor cause the inventory system to:
        energize the beacon tag by the energizing signal;
        receive the first return signal from the beacon tag by the antenna;
        determine a presence of the beacon tag based on the electrical characteristic; and
        store a value of the electrical characteristic of the first return signal in a memory of the RFID tag.

2. The system of claim 1, wherein the electrical characteristic is a resonant frequency of the beacon tag.

3. The system of claim 1, wherein the electrical characteristic includes a ring-down decay rate of the beacon tag.

4. The system of claim 1, wherein the RFID tag includes a unique identifier, and
    wherein the instructions, when executed by the processor, further cause the inventory system to associate the value of the electrical characteristic with the unique identifier.

5. The system of claim 4, wherein the instructions, when executed by the processor, further cause the system to determine an identity of the potentially retained surgical item based on the association between the value of the electrical characteristic and the unique identifier.

6. The system in claim 1, wherein the RFID tag is at least one of a high frequency tag, or an ultra-high frequency tag.

7. The system of claim 1, further comprising a display,
    wherein the instructions, when executed by the processor, further cause the inventory system to display the determined presence of the beacon tag on the display.

8. An inventory system configured for detecting and counting potentially retained surgical items within a body of a patient, the inventory system comprising:
- a beacon tag configured to transmit a first return signal when energized, the first return signal including an electrical characteristic;
- a signal generator configured to generate an energizing signal for the beacon tag;
- an antenna operably coupled to the signal generator, the antenna configured to receive at least the first return signal transmitted by the beacon tag;
- a processor; and
- a memory, including instructions stored thereon, which when executed by the processor cause the inventory system to:
  - energize the beacon tag by the energizing signal;
  - receive the first return signal from the beacon tag by the antenna;
  - determine a presence of the beacon tag based on the electrical characteristic; and
  - determine a quantity of potentially retained surgical items based on the first return signal.

9. The inventory system of claim 8, wherein the electrical characteristic includes a resonant frequency of the beacon tag.

10. The inventory system of claim 8, wherein the electrical characteristic includes a ring-down decay rate of the beacon tag.

11. The inventory system of claim 8, wherein the instructions, when executed by the processor, further cause the system to display the determined presence of the beacon tag on a display.

12. The inventory system of claim 8, wherein the instructions, when executed by the processor, further cause the inventory system to transmit a second return signal, by an RFID tag, the second return signal including the electrical characteristic when energized.

13. The inventory system of claim 12, wherein the instructions, when executed by the processor, further cause the system to store a value of the electrical characteristic of the first return signal in a memory of the RFID tag.

14. The inventory system of claim 13, wherein the RFID tag includes a unique identifier, and
wherein the instructions, when executed by the processor, further cause the system to associate the value of the electrical characteristic with the unique identifier.

15. The inventory system of claim 14, further comprising: wherein the instructions, when executed by the processor, further cause the system to:
- determine an identity of the potentially retained surgical item based on the association between the value of the electrical characteristic and the unique identifier; and
- display the determined identity of the potentially retained surgical item on a display.

16. The inventory system of claim 8, wherein the instructions, when executed by the processor, further cause the inventory system to determine a quantity of potentially retained surgical items based on the first return signal.

17. A non-transitory computer-readable medium storing instructions which, when executed by a processor, cause the processor to perform a method for detecting and counting potentially retained surgical items within a body of a patient, comprising:
- energizing a beacon tag, the beacon tag configured to transmit a return signal including an electrical characteristic when energized;
- receiving the return signal from an antenna, the antenna operably coupled to a signal generator, the antenna configured to receive the return signal transmitted by the beacon tag;
- determining a presence of the beacon tag based on the electrical characteristic; and
- storing a value of the electrical characteristic of the first return signal in a memory of an RFID tag.

* * * * *